US 6,702,758 B2
(12) United States Patent
Iseberg

(10) Patent No.: US 6,702,758 B2
(45) Date of Patent: *Mar. 9, 2004

(54) HAND-HELD HEARING SCREENER APPARATUS

(75) Inventor: Steven J. Iseberg, Palatine, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 301 days.

This patent is subject to a terminal disclaimer.

(21) Appl. No.: 09/973,129

(22) Filed: Oct. 9, 2001

(65) Prior Publication Data

US 2002/0016554 A1 Feb. 7, 2002

Related U.S. Application Data

(63) Continuation of application No. 09/285,938, filed on Apr. 2, 1999, now Pat. No. 6,299,584, which is a continuation-in-part of application No. 08/832,277, filed on Apr. 3, 1997, now Pat. No. 5,954,669.

(51) Int. Cl.$^7$ .................................................. A61B 5/00

(52) U.S. Cl. ......................................... 600/559; 73/585

(58) Field of Search ........................... 600/559; 73/585; 128/864–868

(56) References Cited

U.S. PATENT DOCUMENTS

| 3,295,513 A | | 1/1967 | Dippolito |
| 3,882,848 A | | 5/1975 | Klar |
| 4,057,051 A | | 11/1977 | Kerouac |
| 4,592,370 A | | 6/1986 | Lee |
| 4,687,173 A | | 8/1987 | Genna |
| 5,738,633 A | | 4/1998 | Christiansen |
| 5,954,669 A | * | 9/1999 | Iseberg ....................... 600/559 |

FOREIGN PATENT DOCUMENTS

DE          3320821 C1    1/1985

OTHER PUBLICATIONS

'Distortion–Product OAE Analysis: Is it Ready For Broad Clinical Use?', By John D. Durrant, The Hearing Journal/Nov. 1992, vol. 45, No. 11.

"A Guide to the Effective Use of Otoacoustic Emissions", by Kemp et al., Ear and Hearing, vol. 22, No. 2, 1990.

"Answer To 10 Common Clinical Questions About Otoacoustic Emissions Today", by Hall III et al., The Hearing Journal/Oct. 1993, vol. 46, No. 10.

"Infant Hearing Screening", by Robert Trace, ADVANCE for Speech–Language & Audiologists, Apr. 15, 1996.

"Low Noise Microphone for Cochelear Emissions", by Killion et al., Text of oral paper C1 presented at the 111$^{th}$ meeting of the Acoustical Society of America, May 1996.

(List continued on next page.)

Primary Examiner—Michael A. Brown
(74) Attorney, Agent, or Firm—McAndrews, Held & Malloy, Ltd.

(57) ABSTRACT

A hearing screener apparatus is provided. In one embodiment, the hearing screener comprises a housing, a testing probe and one or microphones mounted with the testing probe. An elastic coupler may be used to suspend the testing probe from the housing. The testing probe may include a shaft and a removable probe tip mounted on the shaft. An ear tip is fitted onto an end of the removable probe tip. The ear tip may have a flexible flange arranged at its end to seal within the ear canal of the patient. The screener allows the testing probe to be manipulated about all axes and may have an isolation body or assembly that acts as the elastic coupler. The elastic coupler provides vibrational noise isolation due to movement of the patient and the user.

22 Claims, 13 Drawing Sheets-

OTHER PUBLICATIONS

"Otoacoustic Emissions: Overview of Measurement Methodologies", by DeVries et al., Seminars In Hearing —vol. 13, No. 1, Feb. 1992.

"Otoacoustic Emissions In Infants and Children: Basic Characteristics And Clinical Application", by Beth A. Prieve, Ph. D., Seminars in Hearing —vol. 13, No. 1, Feb. 1992.

A Review of Otoacoustic Emissions, by Probst et al., J. Acoust. Soc. Am. 89(5), May 1991.

"Screening Infants and Children By Means of TEOAE", by Giebel et al., The Hearing Journal/Nov. 1992, vol. 45, No. 11.

* cited by examiner

HAND-HELD HEARING SCREENER APPARATUS

CROSS-REFERENCE TO RELATED APPLICATIONS

This application is a continuation of U.S. application Ser. No. 09/285,938 filed Apr. 2, 1999, now U.S. Pat. No. 6,299,584 issued Oct. 9, 2001, which is a continuation-in-part of U.S. application Ser. No. 08/832,277 filed Apr. 3, 1997, now U.S. Pat. No. 5,954,669 issued Sep. 21, 1999. The above-referenced applications and patents are hereby incorporated herein by reference in their entirety.

STATEMENT REGARDING FEDERALLY SPONSORED RESEARCH OR DEVELOPMENT

Not Applicable

BACKGROUND OF THE INVENTION

The present invention relates generally to hearing test devices and more specifically to an infant hearing screener which uses distortion-product otacoustic emissions (DPOAE) to determine the function of the outer hair cells, which is an indication of middle-ear function. For example, the absence of DPOAE indicates a possible hearing loss.

The otacoustic emissions produced by a healthy ear are extremely small in magnitude. The emissions typically range from −10 db SPL to +20 db SPL. Any kind of extraneous noise introduced into the ear canal or measurement system can mask these emissions and give a false negative response. The microphone must have a very low internal noise level to discriminate the emissions from the system noise. All existing equipment for testing for DPOAE uses a probe which seals into the ear canal and is attached to the measurement equipment through a cable. This type of system is not practical in an infant screener for several reasons.

These reasons include the fact that an infant's ear canal is very small, and as a result, it can be quite difficult to seal a probe into such a small canal. any pull on the probe from the attached cable can break the seal or pull the probe out of the canal. In addition, the time required to place a probe in the infant's ear canal significantly slows down the testing process. Typically, the infant is asleep when the testing is performed so that movement is minimal. The process of putting the probe into the infant's ear canal in a manner so that it stays for the duration of the test often wakes the infant which, of course makes the test difficult or impossible to perform.

While a hand-held screening device alleviates many of the above discussed problems, implementation of such a device has inherent problems which must be overcome to provide an effective hearing measurement device. One such problem results from the vibrational noise generated by the tester's hand during the testing. This noise is transmitted through the device and into the microphone which prevents accurate measurements. Holding a conventional probe to the ear canal creates a noise level that completely masks any emissions that could otherwise be detected.

Another problem is the difficulty in achieving a consistent seal to the infant's ear canal. Difficulty in maintaining the seal results from minor movements of the infant's head and/or the tester's hand.

Further limitations and disadvantages of conventional and traditional approaches will become apparent to one of skill in the art, through comparison of such systems with the present invention as set forth in the remainder of the present application with reference to the drawings.

BRIEF SUMMARY OF THE INVENTION

The present invention is related to an hearing screener that uses distortion-product otacoustic emissions (DPOAE) to determine the function of the outer hair cells within the middle ear structure. The function of the outer hair cells is an indication of middle-ear function; the absence of DPOAE indicates a possible hearing loss.

In one embodiment, the screener is hand-held device that couples to the infant's ear to perform DPOAE testing. The device creates tones and administers them to the ear canal through two receivers. The emissions are then picked up through a low-noise microphone, and analyzed by a built-in digital signal processor (DSP). The result is displayed on a liquid crystal display (LCD) and can be printed by infrared link to a separate hand-held printer.

Aspects of the present invention may be found in a hearing screener apparatus that comprises a housing, a testing probe operatively coupled to the housing, and one or more microphone(s). In one embodiment, the microphone has a noise floor substantially similar to an industry standard microphone when the housing is grasped by a user. In another embodiment, the microphone has a noise floor of at least approximately 15 dB lower when the housing is grasped by a user than when the testing probe is grasped by a user.

The microphone(s) may be mounted with the testing probe, for example, and the testing probe may be vibrationally isolated from the housing. In one embodiment, the testing probe is elastically coupled to the housing. In addition, the hearing screener apparatus may further comprise an isolation body elastically coupled between the testing probe and the housing. The hearing screener apparatus may also comprise an ear tip mounted on the testing probe for acoustically sealing the ear canal of a test subject.

These and other advantages and novel features of the present invention, as well as details of an illustrated embodiment thereof, will be more fully understood from the following description and drawings.

DETAILED DESCRIPTION OF THE INVENTION

A hearing screener apparatus which uses distortion product otacoustic emissions (DPAOE) to determine the function of the outer hair cells, which is an indicator of middle ear function, is provided. The hearing screener is preferably a hand-held device that couples to an infant's ear to effectively perform DPAOE testing for possible hearing loss. An embodiment of the screener includes an assembly to maintain sealing contact in the ear canal of the patient as well as isolating vibrational noise from their microphone assembly caused by the tester.

Figure 1A:
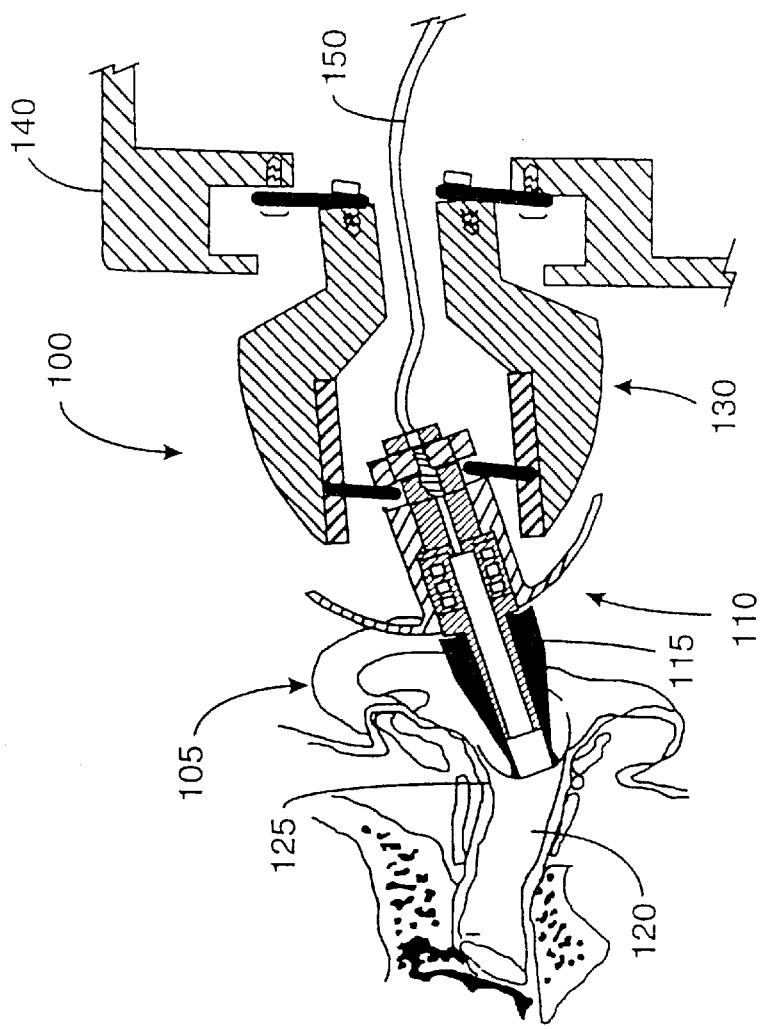
FIG. 1A is a side view in cross-section of an embodiment of the hearing screener arranged in a patient's ear canal.
Figure 1B:
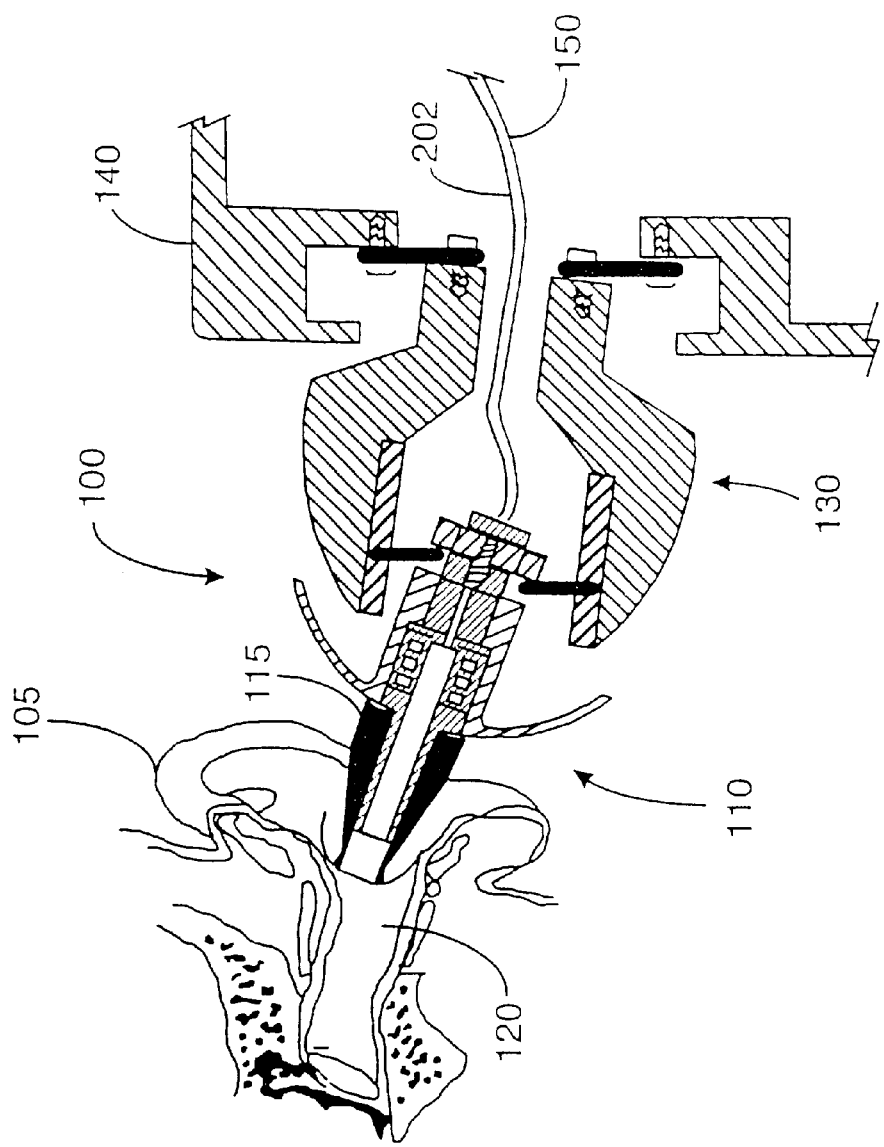
FIG. 1B is a side view in cross-section of an embodiment of the hearing screener arranged in a patient's ear canal.

Referring now to the figures, FIG. 1A is a side view in cross-section of an embodiment of the hearing screener arranged in a patient's ear canal. FIG. 1B is a similar side view of the bearing screener arranged at a different angle of attack into the patient's ear canal. An embodiment of the hearing screener is referenced generally at 100. A patient's ear 105 is also illustrated. The hearing screener 100 includes a testing probe indicated at 110. The testing probe 110 includes an ear tip 115. The ear tip 115 is arranged at the entrance of an ear canal 120 as shown in FIGS. 1A and 1B. As illustrated, the ear tip 115 includes a curved flange 125 to effectively seal the ear canal 120, thus effectively coupling the testing probe 110 of the hearing screener 100 with the patient's ear 105 so that proper testing can be performed.

FIGS. 1A and 1B also include an isolation body 130 and a housing 140. Also, a connection 150 is illustrated. The components of the hearing screener 100 are described in more detail below with reference to FIGS. 2 and 3.

Figure 2:
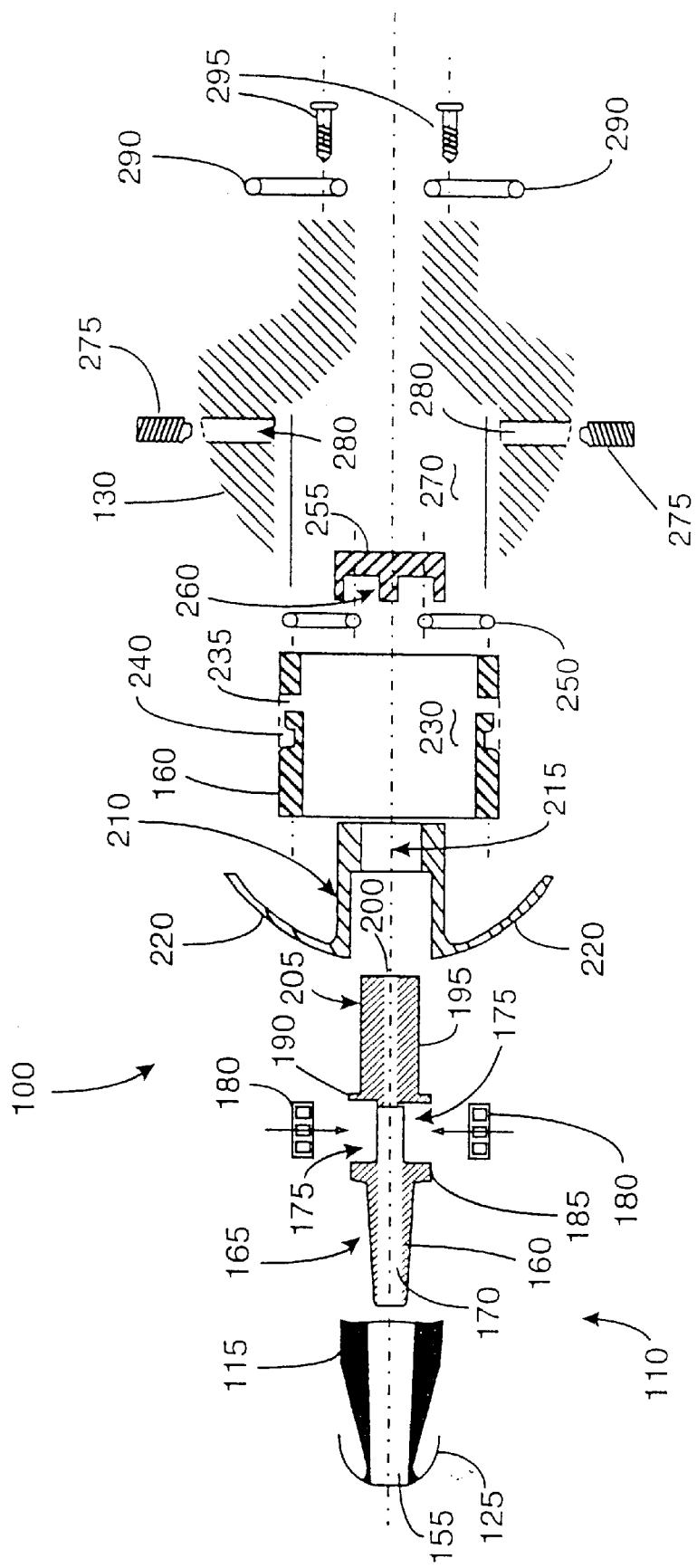
FIG. 2 is an exploded cross-sectional side view of an embodiment of the present invention.

FIG. 2 illustrates an exploded side view of an embodiment of the hearing screener 100 of the present invention. For clarity, the housing 140 is not shown in FIG. 2. As discussed above, the hearing screener 100 includes the testing probe 110, the isolation body 130 and a cylindrical coupling sleeve 160 disposed between the probe 110 and the body 130.

Proceeding from left to right in FIG. 2, the hearing screener 100 comprises the ear tip 115 having the curved flange 125 to enable proper sealing within a patient's ear canal as illustrated in FIGS. 1A and 1B and described above. The curvature of the flange 125 permits the ear tip 115 to be arranged at various angles in the patient's ear canal 120 as shown in FIGS. 1A and 1B. This is beneficial when the patient moves or when the tester needs to position the screener 100 at the proper angle for taking accurate readings. The ear tip 115 also includes a longitudinal throughbore 155. The throughbore 155 is dimensioned to accept a first end 160 of a microphone housing 165. The first end 160 of the microphone housing 165 includes a longitudinal cavity 170. The microphone housing 165 also includes a recess 175 for receiving a microphone 180 therein. FIG. 2 illustrates an embodiment in which two microphones are used. However, one or more microphones may be used in the present invention. The microphones 180 are held in the recess 175 which is defined by a first shoulder 185 and a second shoulder 190. The shoulders 185, 190 protect the microphones 180 as well as provide a defined volume in which the microphones 180 may be located. The microphone housing 165 also includes a cylindrical second end 195 having a bore 200. The bore 200 is designed to receive the connection 150 (see FIG. 1) which preferably includes one or more sound tubes 202 (see FIG. 4A) and electrical connectors 204 for transmitting electrical signals from the microphones 180. In addition, the cylindrical second end 195 of the microphone housing 165 includes a circumferential notch 205. The notch 205 is explained further below with reference to FIG. 3.

Continuing to the right of FIG. 2, the hearing screener 100 also includes a microphone housing support member 210 having a through hole 215 for receiving the second end 195 of the microphone housing 165 therethrough. The support member 210 also includes a curved flange 220. The flange 220 acts as a shield to prevent debris from entering the various components of the hearing screener 100. The shielding ability is illustrated in more detail in FIG. 3, in which the hearing screener 100 is assembled.

In addition, the cylindrical coupling sleeve 160 is shown in FIG. 2. The coupling sleeve 160 has a open interior 230. An L-shaped notch 235 having a cavity 240 is also illustrated. A plurality of o-rings 250 fit within the L-shaped notch 235 and are seated in the cavity 240. In addition, a retaining cap 255 is provided. The retaining cap 255 slips over the cylindrical second end 195 of the microphone housing 165 as illustrated more filly in FIG. 3 and captures the o-rings 250 by tabs 260 formed in the retaining cap 255.

Also shown in FIG. 2 is the isolation body 130 which has a cylindrical bore 270 for receiving the cylindrical coupling sleeve 160 therein. The coupling sleeve 160 is held securely in the isolation body 130 by set screws 275 which are tightened into threaded holes 280 formed in the isolation body 130. A second set of o-rings 290 is secured to the isolation body 130 by screws 295. The screws 295 bore into the isolation body 130. Further, the exploded assembly of FIG. 2 is illustrated in an assembled state in FIG. 3.

Figure 3:
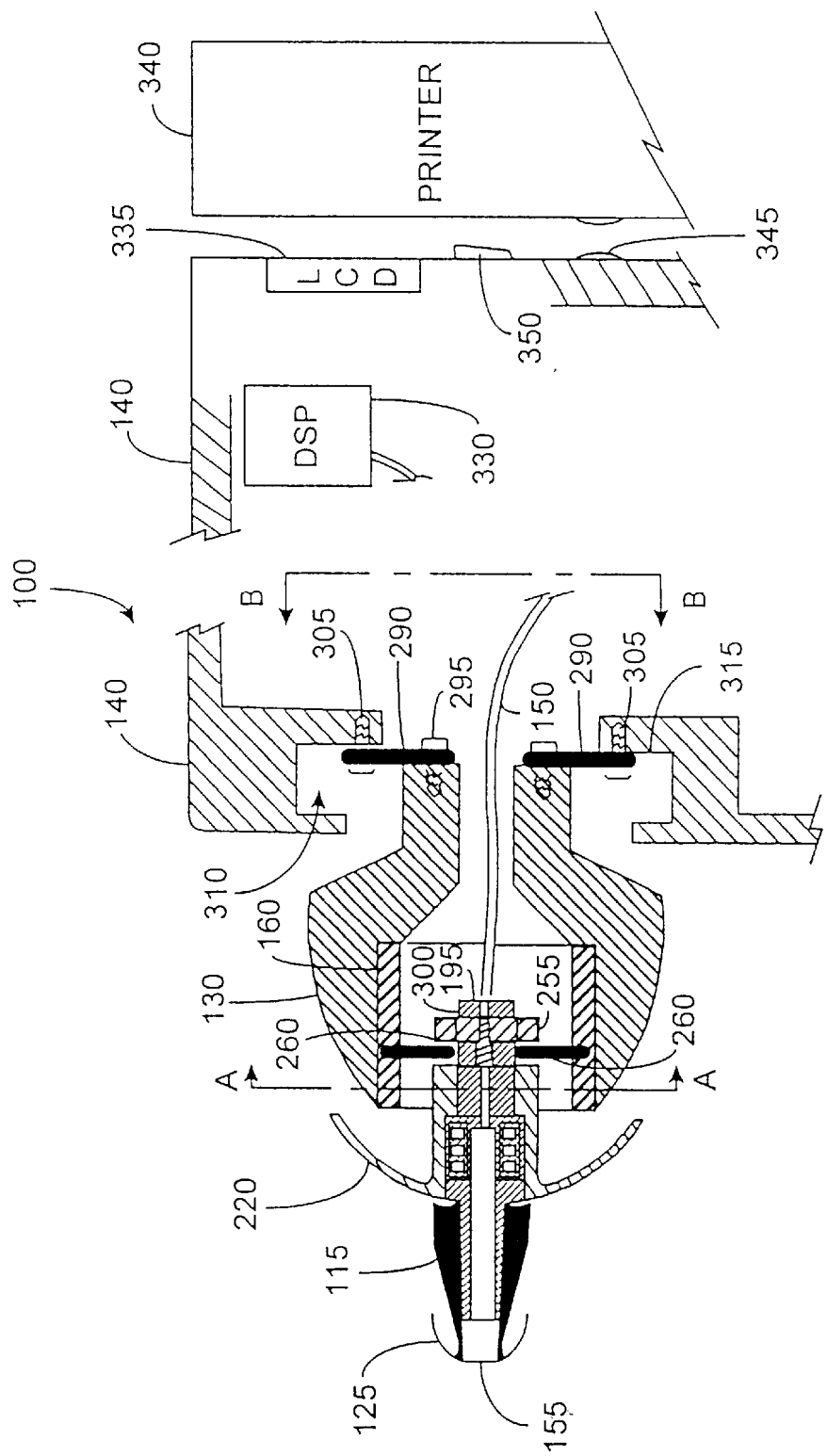
FIG. 3 illustrates a cross-sectional side view of an embodiment of a hearing screener of the present invention.

FIG. 3 illustrates an assembled embodiment of the hearing screener 100 of the present invention wherein like parts are represented by like numerals. As illustrated, when the components are assembled, the first end 160 of the microphone housing 165 fits inside the throughbore 155 of the ear tip 115. In addition, the microphone housing 165 fits in the through hole 215 of the microphone housing support member 210. In particular, the second end 195 of the microphone housing 165 passes through the support member 210 and the retaining cap 255 so that the circumferential notch 205 located adjacent the second end 195 of the microphone housing 165 is exposed past the retaining cap 255. Thus, a retaining clip 300 can be clipped around the second end 195 of the microphone housing 165 and reside within the circumferential notch 205 to secure the testing probe 110 assembly together.

As illustrated, the o-rings 250 are secured at one end by the cylindrical coupling sleeve 160 and at the other end by the retaining cap 255. In particular, one end of each o-ring 250 is held in the cavity 240 of the L-shaped notch 235 of the cylindrical coupling sleeve 160. Another end of each o-ring is held by tabs 260 of the retaining cap 255. The second set of o-rings 290 is also illustrated in a connected state in FIG. 3. The screws 295 hold one end of the o-ring 290 to the isolation body 130. In addition, screws 305 secure the other end of the o-rings 290 to the housing 140. The housing 140 also has a cavity 310 and a mounting surface 315. The screws are preferably screwed into the mounting surface 315 of the housing 140.

FIG. 3 schematically illustrates further components of the hearing screener 100. For example, a digital signal processor 330 is built into the housing 140. Also an LCD display 335 is arranged in the housing to provide measurement data as a display to the user. Further, a printer 340 may be used to print out data obtained during the hearing testing. The printer 340 is preferably a small infrared type printer. Also, an infrared connection 345 between the hearing screener 100 and the printer 400 is provided. Also operator control 350 are provided on the housing 140.

FIG. 3 illustrates the hearing screener 100 in a position in which the longitudinal axes of the components is perpendicular to the housing 140. The two sets of o-rings 250, 290 provide free movement about all axes for the testing probe portion 110 of the screener 100, as well as the isolation body 130. However, as FIGS. 1A and 1B indicate, the testing probe 110 can be displaced at an angle relative to the isolation body 130, which in turn can also be displaced at an angle relative to the housing 140. Such compound angular displacements advantageously provide manipulation of the hearing screener 100 to facilitate easy use of the device. Such manipulation capability is provided by the arrangement of the o-rings 250, 290. Embodiments of the arrangement for the o-rings are illustrated in FIGS. 4A and 4B.

Figure 4B:
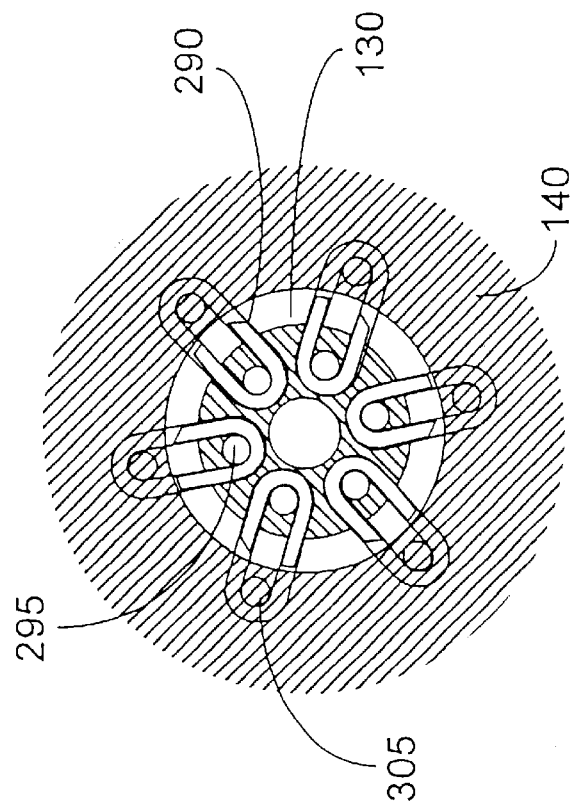
FIG. 4B is a cross-sectional view of a portion of the hearing screener taken along line B—B of FIG. 2.
Figure 4A:
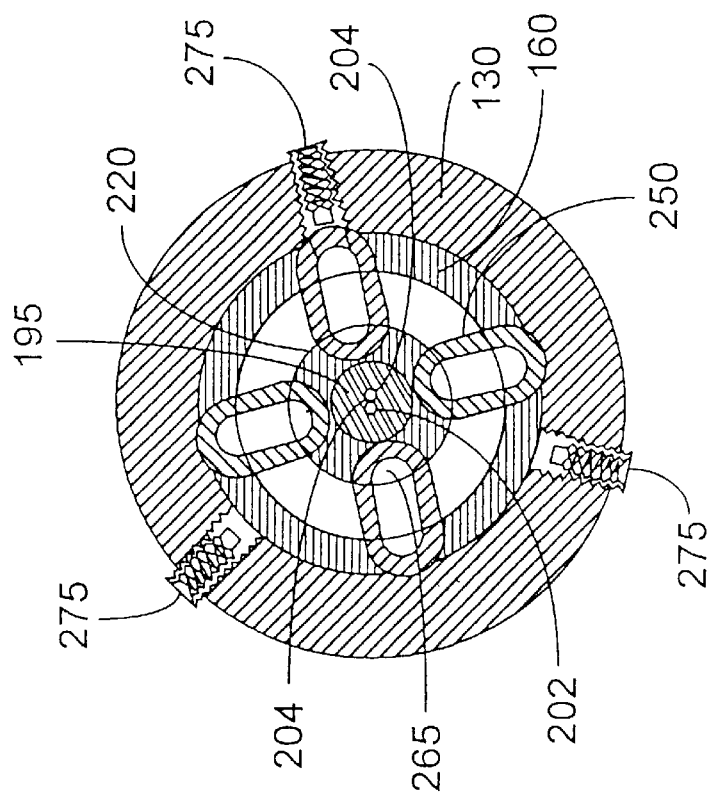
FIG. 4A is a cross-sectional view of a portion of the hearing screener taken along line A—A of FIG. 2.

For example, FIG. 4A illustrates a cross-section view of the arrangement of o-rings 250 which connect the microphone housing 165 to the coupling sleeve 160 within the isolation body 130. FIG. 4A is taken along section line A—A in FIG. 3. As shown, four o-rings 250 are equally distributed between coupling sleeve 160 and the second end 195 of the microphone housing 165. In this manner, the microphone housing 165 is concentrically suspended within the coupling sleeve 160. As discussed above, one end of the o-ring 250 is held within the coupling sleeve 160 by being captured within the L-shaped notch 235 and residing in the recess 240. The other end of the o-ring 250 is captured by the tab 260, which is part of the retaining cap 255. Also, the coupling sleeve 160 is maintained within isolation body 130 by the set screws 275. The set screws 275 are tightened down within the screw holes 280 to secure the sleeve 160 within the isolation body 130.

FIG. 4B also illustrates the plurality of o-rings 290 distributed between the isolation assembly 130 and the housing 140. FIG. 4B is taken along section line B—B of FIG. 3. As illustrated, six o-rings 290 are mounted by screws 295 which attach to the isolation body 130 and screws 305 which attach to the mounting surface 315 of the housing 140. The isolation body 130 is thus concentrically suspended within the housing 140 by the six o-rings 290. As illustrated in FIGS. 4A and 4B, the number of o-rings may be chosen for a particular application. Also, the elasticity of the o-rings may be selected for a particular use and resiliency desired. In a preferred embodiment, o-rings of 70 durometer SHORE A provide a sufficient resiliency and feel. However, the number and elasticity of the o-rings may be chosen depending on the application desired.

Figure 5:
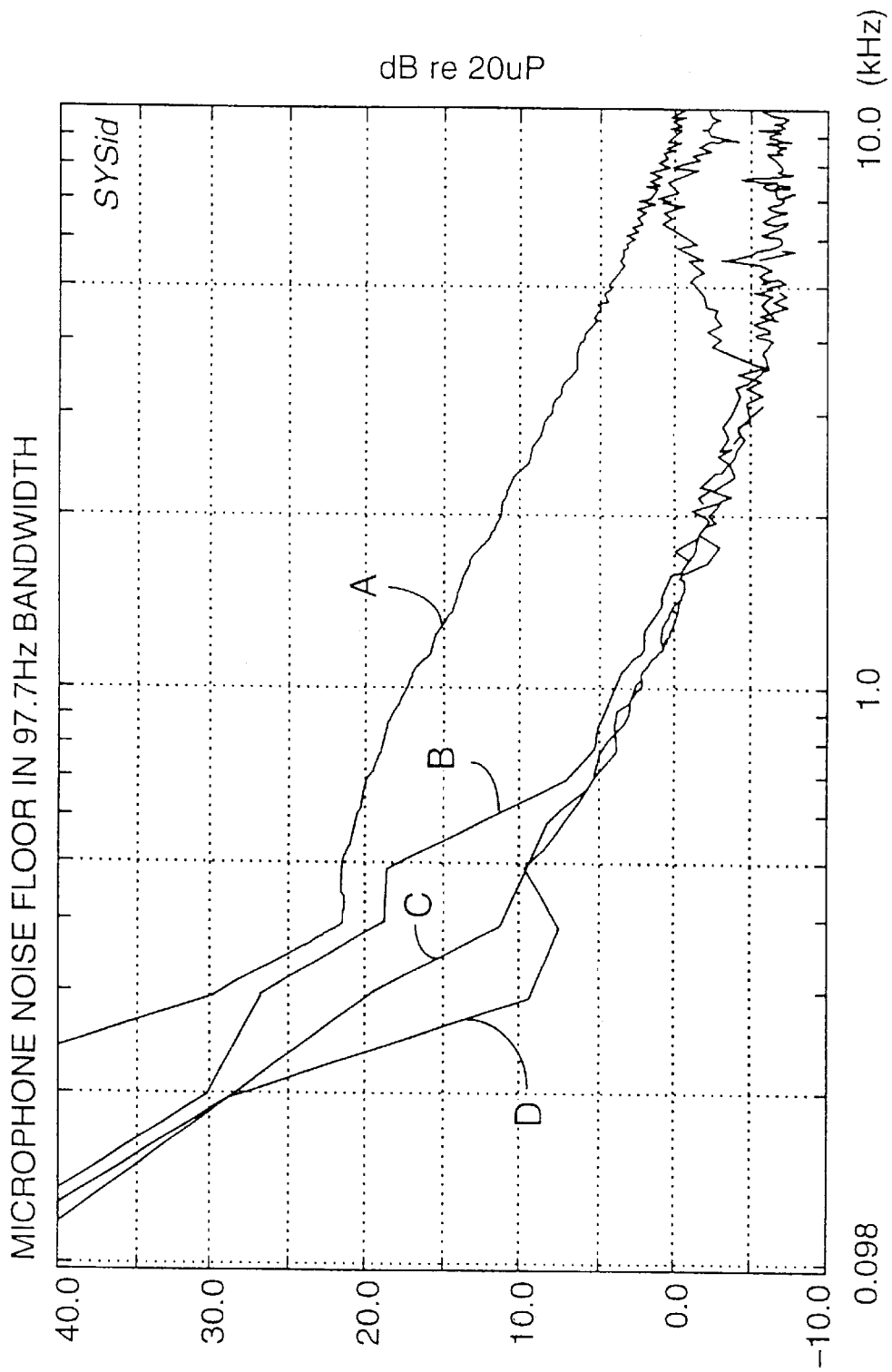
FIG. 5 is a graph illustrating various microphone noise floor levels of the present invention.

As set forth above, vibrations caused by the user holding onto the screener apparatus 100 are translated into noise. An advantage of the present invention is a dampening of this noise so that it does not interfere with the measurements being taken. FIG. 5 graphically illustrates how this elimination of the vibrational noise is accomplished.

FIG. 5 is a graph illustrating microphone noise various curves plotted for different measurement situations. The Y axis is dB and the X axis is frequency in kilohertz (kHz). The various curves illustrate experimental data taken as different parts of the hearing screener 100 are held by a tester. For example, curve A illustrates the microphone noise floor with the tester holding the ear tip 115 assembly of the hearing screener 100. Thus, the first set of o-rings 250 and the second set of o-rings 290 are rendered inoperable. Similarly, curve B illustrates the microphone noise floor when the tester holds the isolation assembly 130 of the hearing tester 100. In this situation, the first set of o-rings 250 is operable, but the second set of o-rings 290 is not. Finally, curve C illustrates a microphone noise floor curve when the tester holds the hearing screener 100 by the housing 140 as intended during a typical use. Thus, both sets of o-rings 250, 290 are operable.

As a basic reference, curve D illustrates the microphone noise for a microphone, such as an ER-10C microphone. The ER-10C microphone has the same effective noise floor as an industry standard microphone. Thus, FIG. 5 illustrates that the isolation effects of the o-rings 250 and 290, along with the arrangement of the preferred embodiment discussed above, yields a microphone noise floor virtually identical to that of the industry standard microphone when the hearing screener 100 is held by the housing 140 as illustrated in curve C. Curve A illustrates that holding the ear tip assembly 115 of the hearing screener 100 prevents the benefits of the o-rings 250, 290 from being exploited. As a result, the noise floor is approximately 15 dB more than that experienced in curve C.

Thus, as described above and graphically illustrated in FIG. 5, the first set of o-rings 250 isolate movements of the patient which cause noise, and the second set of o-rings 290 isolate hand vibration which causes noise. Together, the reduction in noise is sufficient for allowing the hand-held hearing screener 100 of the preferred embodiment discussed above to be used for taking accurate measurements of otacoustic emissions.

Figure 6:
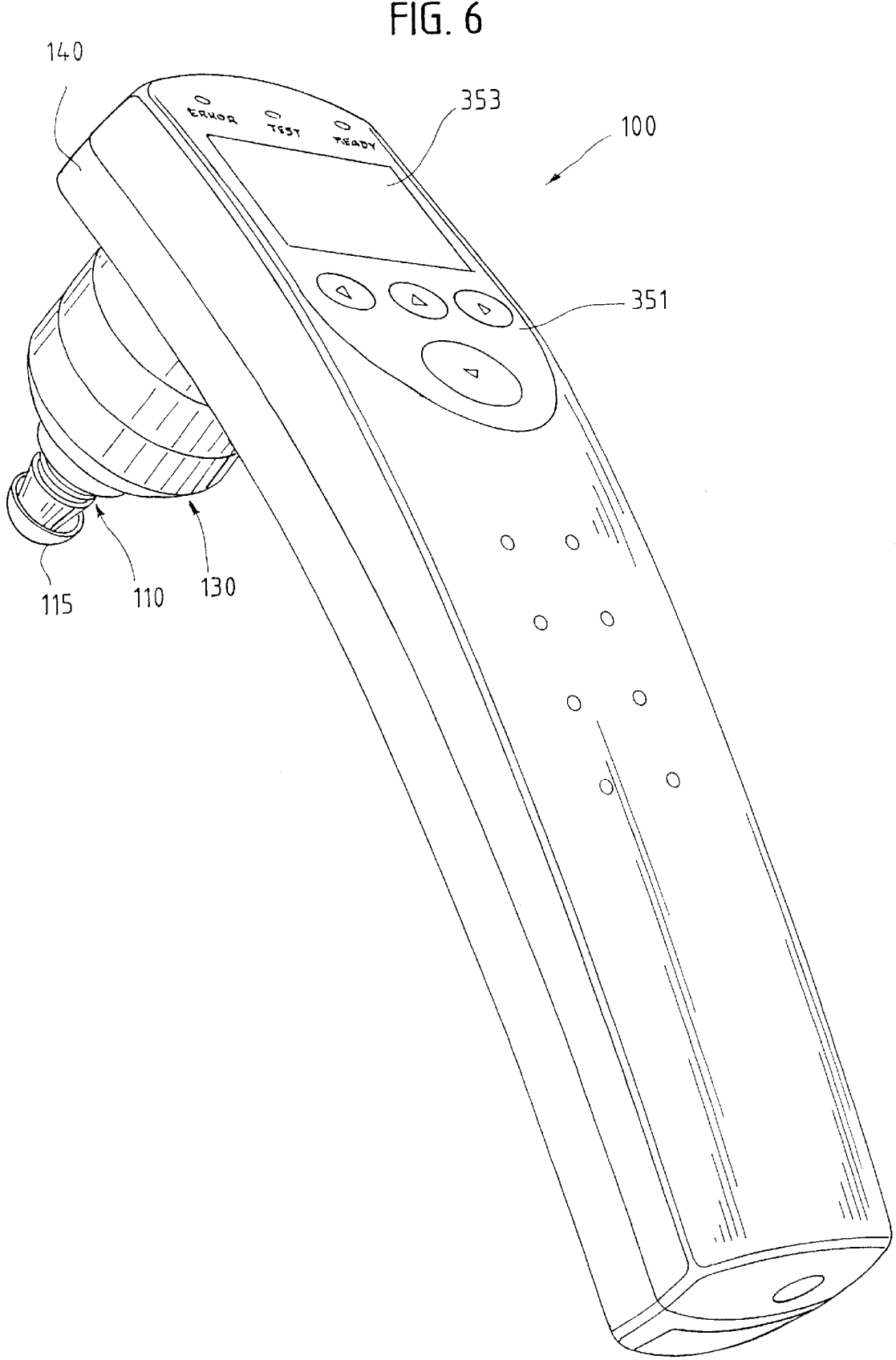
FIGS. 6 and 7 illustrate another embodiment of the hearing screener built in accordance with the present invention.
Figure 7:
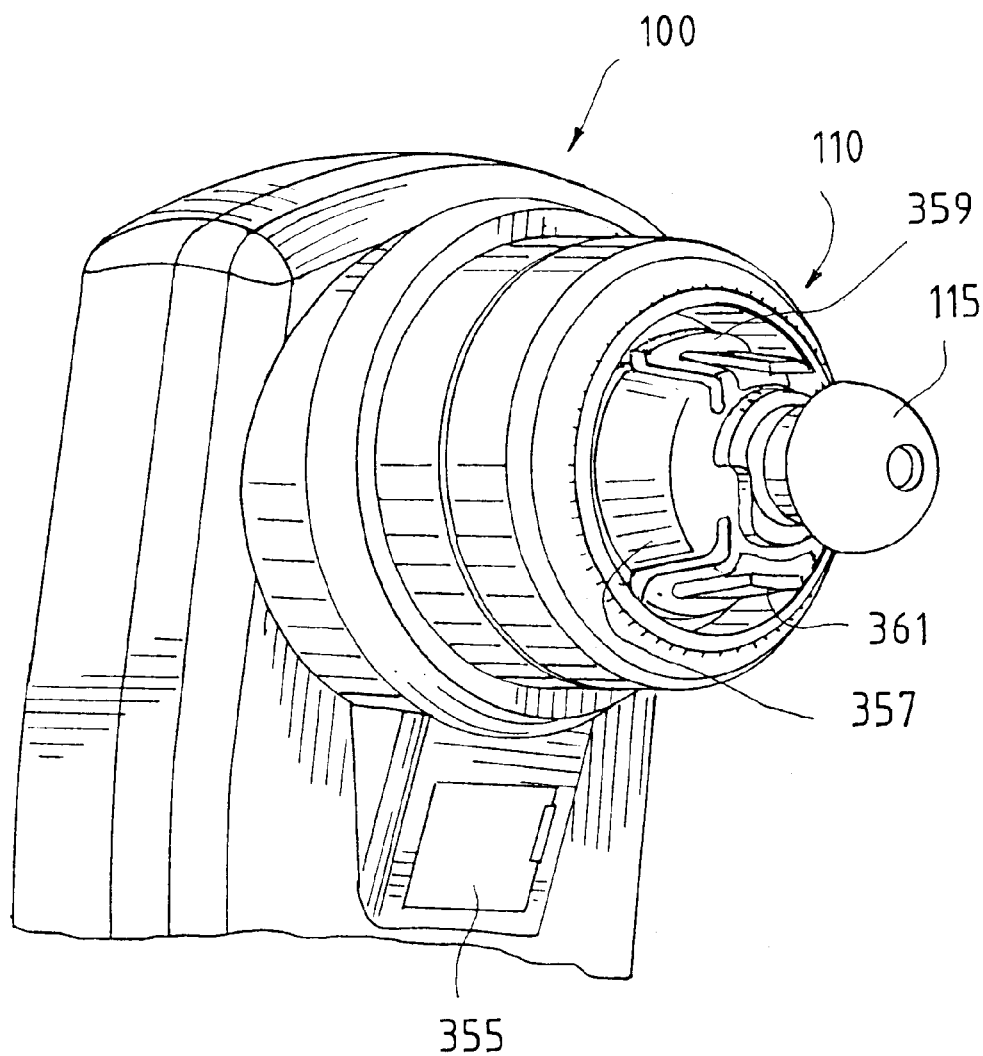

FIGS. 6 and 7 illustrate another embodiment of the hearing screener 100 built in accordance with the present invention. The hearing screener 100 includes a housing 140, an isolation body or assembly 130 and a testing probe 110. As explained more completely above and below, the isolation body 130 acts as, for example, an elastic coupler that suspends the testing probe 110 from the housing 140. As discussed above, testing probe 110 includes ear tip 115.

The housing 140 includes a keyboard 351 for entry of commands, and a screen 353 for display of data. The screen 353 may be the same as LCD screen 335 discussed above. The housing 140 also includes a serial port 355 (see FIG. 7) for communication of data to a printer (not shown) or to a suitable docking station (not shown) that may be connected to a printer, for printout of data obtained during the hearing testing. The serial port 355 may also be used to communicate data directly to a personal computer.

Referring to FIG. 7, testing probe 110 includes a removable probe tip 357. Probe tip 357 is removed by pressing tabs 359 and 361. Details regarding probe tip 357 are discussed below with respect to FIGS. 12A and 12B.

Figure 8:
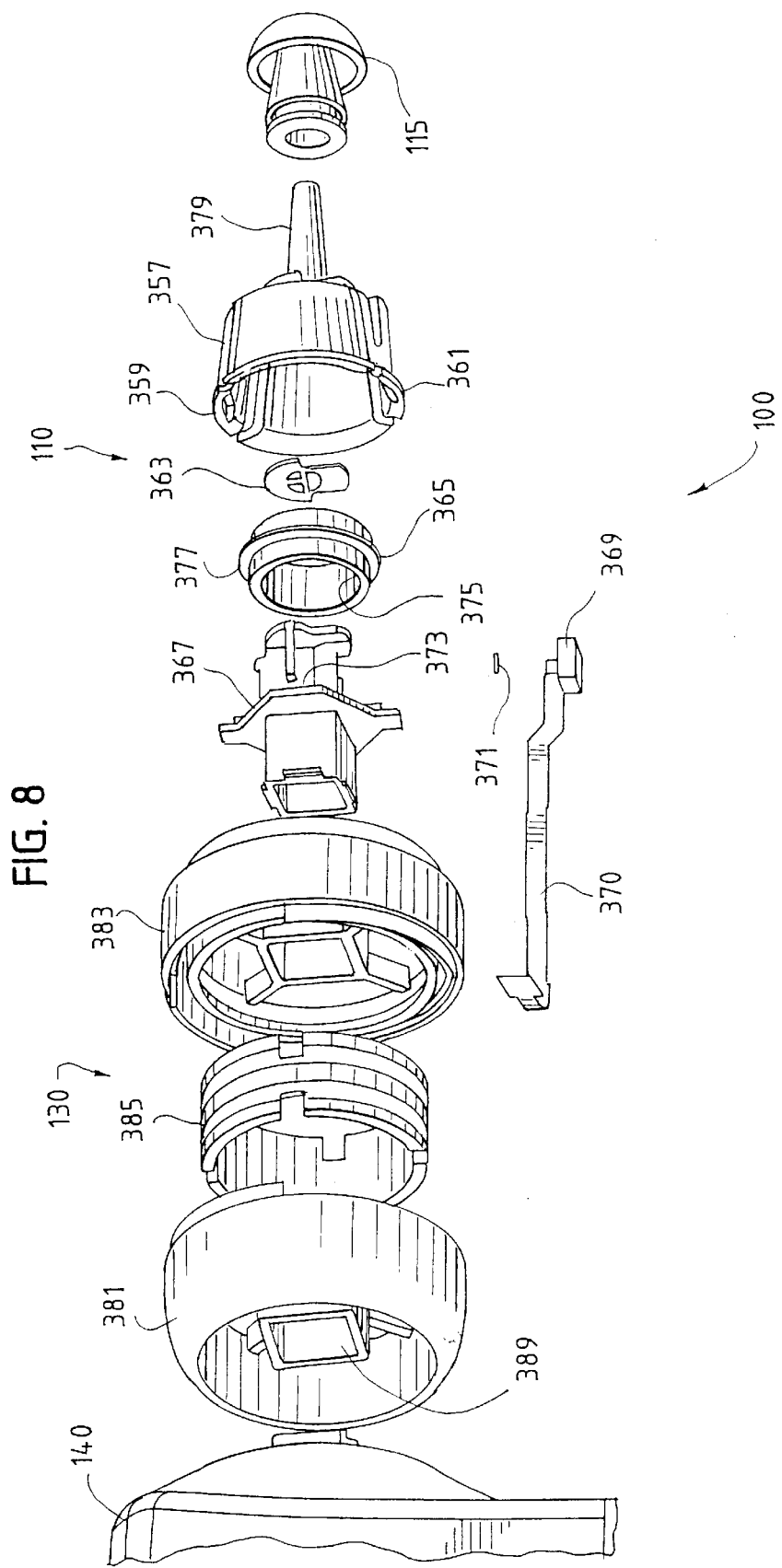
FIG. 8 is an exploded view of the hearing screener of FIGS. 6 and 7.

FIG. 8 is an exploded view of the hearing screener 100 of FIGS. 6 and 7. Testing probe 110 of FIGS. 6 and 7 is comprised of removable probe tip 357, seal 363, retainer 365 and shaft 367. A port (note shown) of microphone 369 is inserted into shaft 367 and a seal 371 provides an acoustic seal between the microphone 369 and the shaft 367. Upon assembly, microphone 369 rests adjacent an outer surface 373 of shaft 367 and is retained by an inner surface 375 of retainer 365. Retainer 365 acts as a fulcrum point for tabs 359 and 361 of removable probe tip 357. Eartip 115 fits over a nose portion 379 of removable probe 357.

Isolation body or assembly 130 of FIGS. 6 and 7 is comprised of springs 381 and 383 and cylinder 385. Springs 381 and 383 maybe identical. Isolation body or assembly 130 attaches to housing 140 and testing probe 110 as discussed below.

Figure 9A:
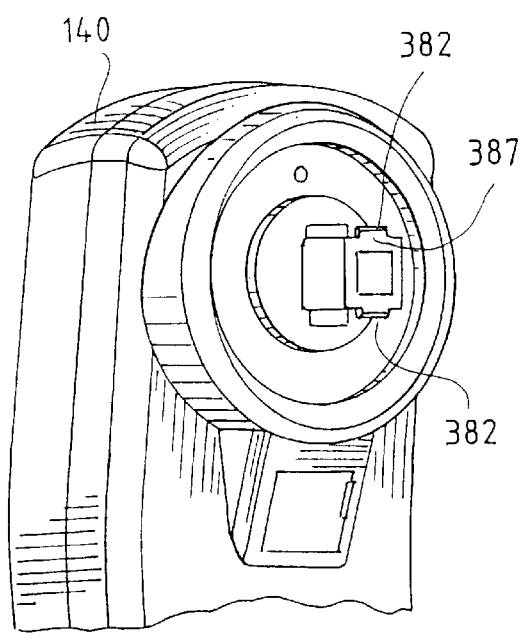
FIGS. 9A, 9B and 9C illustrate mounting of an isolation body or assembly onto a housing of the screener in accordance with the present invention.
Figure 9B:
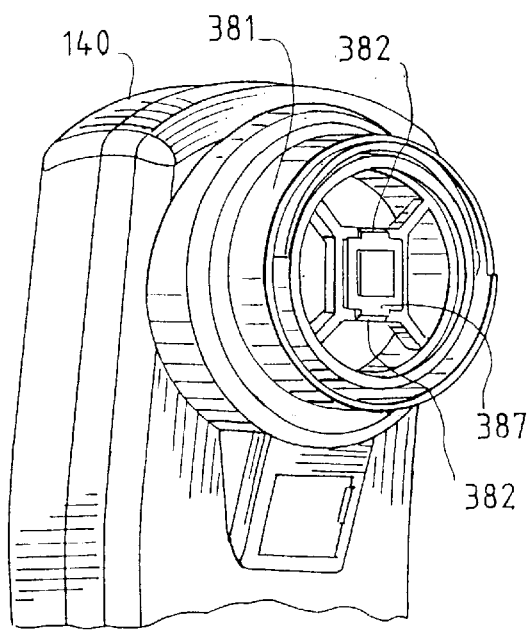
Figure 9C:
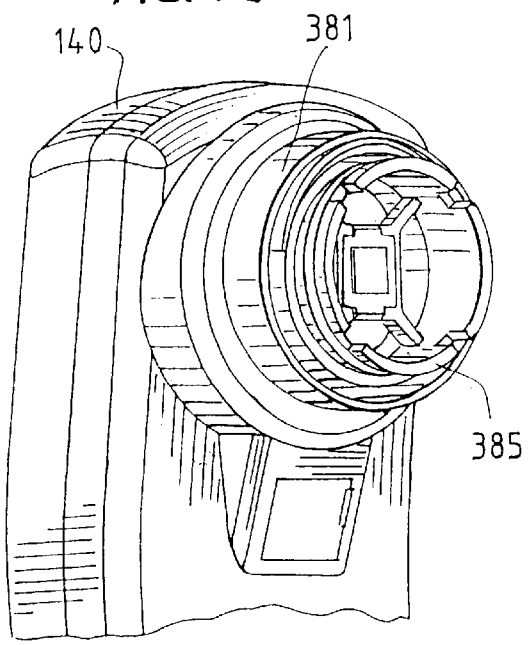

FIGS. 9A, 9B and 9C illustrate mounting of the isolation body or assembly 130 onto the housing 140. FIG. 9A shows housing 140 having a mounting extension 387 protruding therefrom. FIG. 9B shows spring 381 mounted on the housing 140 via mating engagement of mounting extension 387 into a recess 389 (see FIG. 8) of spring 381. Mounting extension 387 includes retaining tabs 382 that releasably lock the spring 381 onto mounting extension 387 of the housing 140. FIG. 9C illustrates the assembly of FIG. 9B further mounting cylinder 385 thereon.

Figure 10:
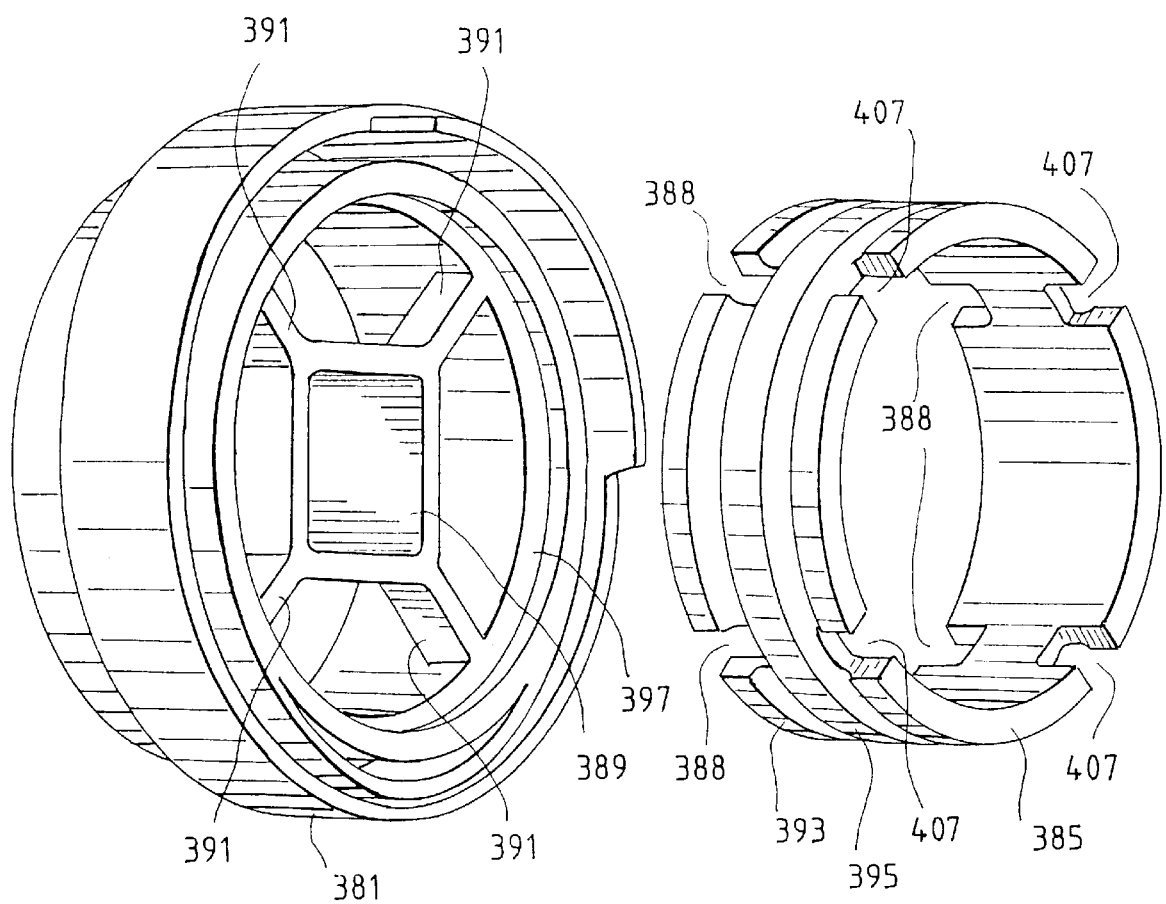
FIG. 10 illustrates more detail of the isolation body or assembly wherein a cylinder is mounted onto a spring in accordance with the present invention.

FIG. 10 illustrates more detail of the mounting of cylinder 385 onto spring 381. Cylinder 385 includes notches 388 that engage couplers 391 of spring 381. Spring 381 is preferably made of an elastomer type material. Couplers 391 therefore provide elastic mounting of the cylinder 385 in spring 381.

Cylinder 385 further includes grooves 393 and 395. Groove 393 of cylinder 385 receives and engages ring 397 of spring 381, thereby mounting and releasably retaining the cylinder 385 on the spring 381.

Figure 11A:
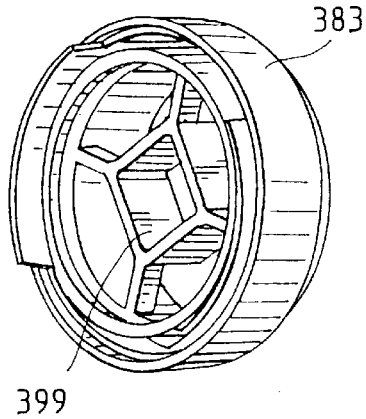
FIGS. 11A, 11B and 11C illustrate mounting of a testing probe on a spring of the isolation body or assembly in accordance with the present invention.
Figure 11B:
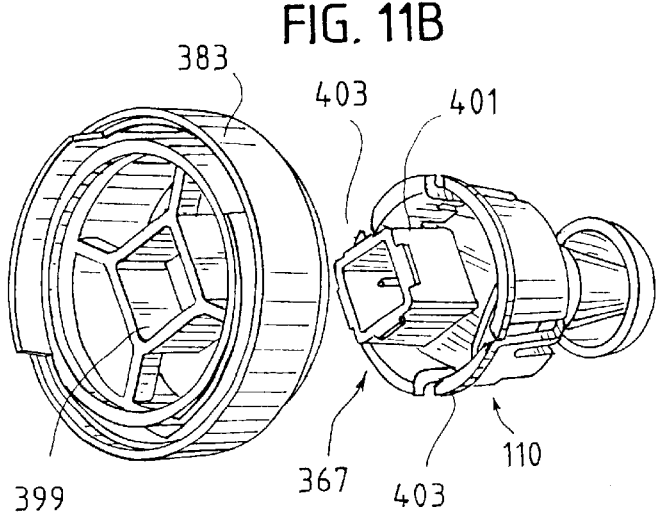
Figure 11C:
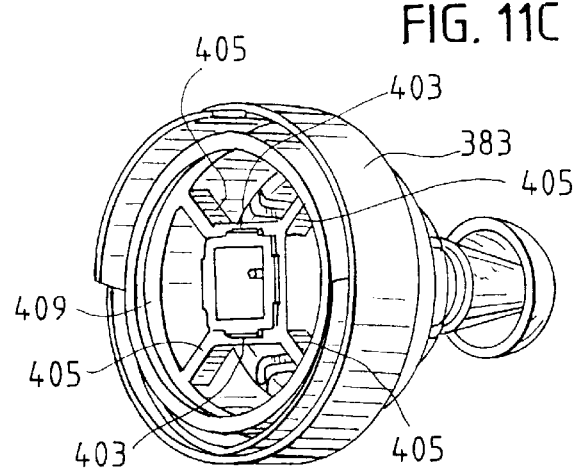

FIGS. 11A, 11B and 11C illustrate mounting of the testing probe 110 on the spring 383. Similar to spring 381 as discussed above, spring 383 includes a recess 399 that matingly engages a mounting extension 401 of shaft 367. Shaft 367 includes retaining tabs 403 to releasable lock spring 383 onto the mounting extension 401 of shaft 367. As can be seen in FIG. 11C, spring 383 includes couplers 405 that engage notches 407 of cylinder 385 (see FIG. 10). Spring 383 further includes ring 409 that engages groove 395 of cylinder 385, thereby mounting and releasably retaining spring 383 on cylinder 385.

The assembly discussed above with respect to FIGS. 9–11 provides elastic coupling of the testing probe 110 to the housing 140 while preventing direct contact between the testing probe 110 and the housing 140. Such a configuration assists in reducing the transmission of vibration from the housing 140 to the testing probe 110. Isolation assembly 130 further enables movement of the testing probe 110 relative to the housing 140 for ease of manipulation during testing, as described above. In addition, the testing probe 110 may be moved relative to the isolation assembly 130, and the isolation assembly 130 may be moved relative to the housing 140, thereby providing further ease of manipulation and vibration dampening.

As discussed above with respect to FIG. 8, microphone 369 is mounted in testing probe 110. Microphone 369 is electrically connected to suitable circuitry within the housing 140 via ribbon cable 370. Upon assembly, ribbon cable 370 extends through shaft 367, cylinder 385 and mounting extension 387 into the housing 140.

Figure 12A:
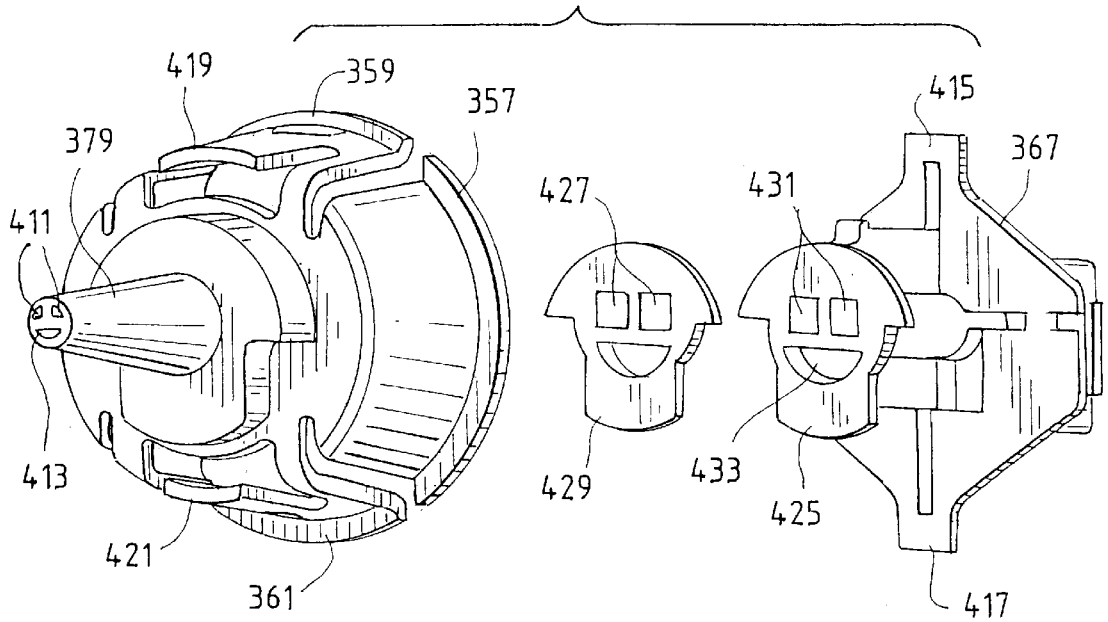
FIGS. 12A and 12B illustrate additional detail of a removable probe tip of the testing probe in accordance with the present invention.
Figure 12B:
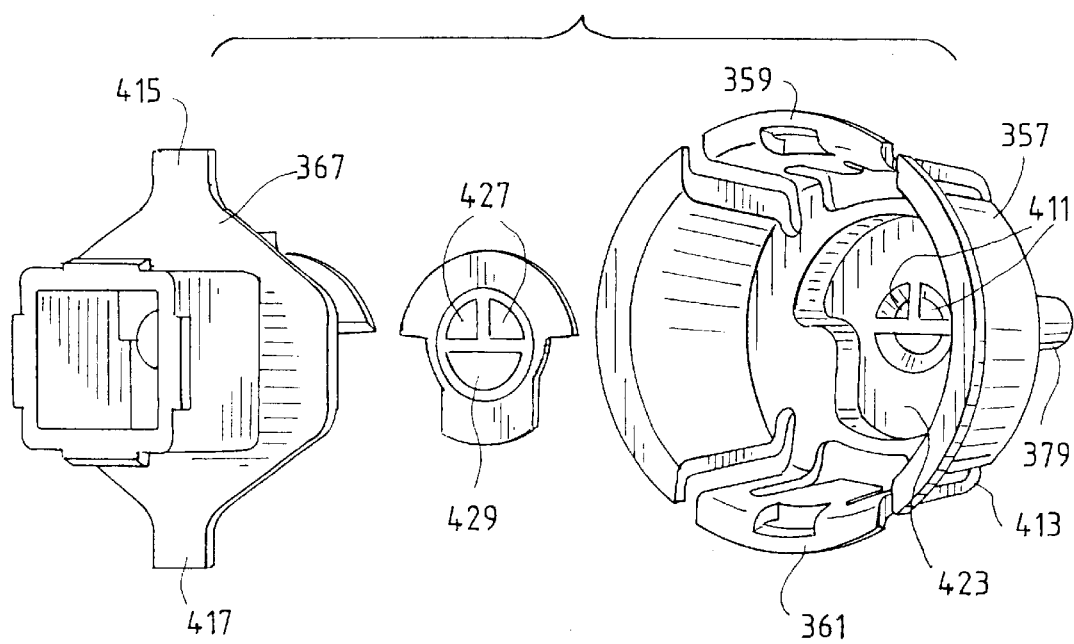

FIGS. 12A and 12B illustrate additional detail of the removable probe tip 357. During testing, sound is presented into the ear canal of a subject via nose portion 379 of the removable probe tip 357, and particularly through channels 411 in nose portion 379. The sound is generated by speakers contained within the housing 140 and transmitted to the channels 411 via flexible sound tubes (not shown) and via fixed tubes 431 and 433 in the shaft 367. Upon assembly, the flexible sound tubes connect to the fixed tubes and extend from the shaft 367, through cylinder 385 and mounting extension 387 into the housing 140, like the ribbon cable 370 discussed above.

Signals from the ear canal are received by microphone 369 via channel 413 in nose portion 379 of removable probe tip 357. Those signals are transduced by the microphone 369 and transmitted to the housing 140.

Channels 411 and 413 of the nose portion 379 of probe tip 357 often become clogged with earwax or other debris, which results in testing failure. Consequently, it is desirable that probe tip 357 be removable from the shaft 367 for cleaning and/or replacement of the probe tip 357. As mentioned above, probe tip 357 includes tabs 359 and 361 for removable engagement of the probe tip 357 on the shaft 367. More particularly, shaft 367 includes protruding members 415 and 417 that engage slots in the tabs 359 and 361, respectively. The probe tip 357 is removed from the shaft 367 by depressing portions 419 and 421 of tabs 359 and 361, respectively.

Upon assembly, seal 363 is trapped between an inner surface 423 of probe tip 357 and an outer surface 425 of shaft 367. Seal 363 includes openings 427 and 429 that acoustically couple the channels 411 and 413 respectively, to tubes 431 and 433 in shaft 367. Seal 363 also provides an acoustic seal between the surfaces 423 and 425. Seal 363 may, for example, be made of an elastomer type material to conform to the surfaces 423 and 425.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A hearing screener apparatus comprising:
    a housing;
    a testing probe operatively coupled to the housing; and
    at least one microphone, the microphone having a noise floor substantially similar to an industry standard microphone when the housing is grasped by a user.

2. The hearing screener apparatus of claim 1 wherein the at least one microphone is mounted with the testing probe.

3. The hearing screener apparatus of claim 2 wherein the testing probe is vibrationally isolated from the housing.

4. The hearing screener apparatus of claim 2 wherein the testing probe is elastically coupled to the housing.

5. The hearing screener apparatus of claim 4 further comprising an isolation body elastically coupled between the testing probe and the housing.

6. The hearing screener apparatus of claim 1 further comprising an ear tip mounted on the testing probe for acoustically sealing the ear canal of a test subject.

7. The hearing screener apparatus of claim 1 wherein the hearing screener performs DPOAE testing.

8. A hearing screener apparatus comprising:
    a housing;
    a testing probe operatively coupled to the housing; and
    at least one microphone, the at least one microphone having a noise floor of at least approximately 15 dB lower when the housing is grasped by a user than when the testing probe is grasped by a user.

9. The hearing screener apparatus of claim 8 wherein the at least one microphone is mounted with the testing probe.

10. The hearing screener apparatus of claim 9 wherein the testing probe is vibrationally isolated from the housing.

11. The hearing screener apparatus of claim 9 wherein the testing probe is elastically coupled to the housing.

12. The hearing screener apparatus of claim 11 further comprising an isolation body elastically coupled between the testing probe and the housing.

13. The hearing screener apparatus of claim 8 further comprising an ear tip mounted on the testing probe for acoustically sealing the ear canal of a test subject.

14. The hearing screener apparatus of claim 8 wherein the hearing screener performs DPOAE testing.

15. A hearing screener apparatus comprising:

a housing;

a testing probe operatively coupled to the housing; and at least one microphone mounted with the testing probe, the testing probe being coupled to the housing such that the at least one microphone is vibrationally isolated from the housing.

16. The hearing screener apparatus of claim 15 wherein the testing probe is elastically coupled to the housing.

17. The hearing screener apparatus of claim 15 wherein the testing probe is vibrationally isolated from the housing.

18. The hearing screener apparatus of claim 17 further comprising an isolation body elastically coupled between the testing probe and the housing.

19. The hearing screener apparatus of claim 15 further comprising an ear tip mounted on the testing probe for acoustically sealing the ear canal of a test subject.

20. The hearing screener apparatus of claim 15 wherein the hearing screener performs DPOAE testing.

21. The hearing screener apparatus of claim 15 wherein the at least one microphone has a noise floor substantially similar to an industry standard microphone when the housing is grasped by a user.

22. The hearing screener apparatus of claim 15 wherein the at least one microphone has a noise floor of at least approximately 15 dB lower when the housing is grasped by a user than when the testing probe is grasped by a user.

* * * * *